(12) United States Patent
Helmer et al.

(10) Patent No.: US 6,203,321 B1
(45) Date of Patent: Mar. 20, 2001

(54) BACKFLOW PREVENTION SYSTEM IN SUCTIONING APPARATUS

(76) Inventors: Kevin Helmer, 7060 Jamaca Ave.; Richard Bushman, 10975 Stone Bridge Trail North, both of Stillwater, MN (US) 55082

(*) Notice: Subject to any disclaimer, the term of this patent is extended or adjusted under 35 U.S.C. 154(b) by 0 days.

(21) Appl. No.: 09/458,246

(22) Filed: Dec. 9, 1999

Related U.S. Application Data

(63) Continuation-in-part of application No. 08/867,752, filed on Jun. 3, 1997, now abandoned.
(60) Provisional application No. 60/019,090, filed on Jun. 3, 1996.

(51) Int. Cl.$^7$ .................................................. A61C 17/06
(52) U.S. Cl. ............................ 433/95; 604/247; 604/902
(58) Field of Search ................................. 433/91, 95, 96; 604/35, 119, 247, 902; 137/539, 855, 857

(56) References Cited

U.S. PATENT DOCUMENTS

| | | |
|---|---|---|
| 2,378,613 | 6/1945 | Young et al. . |
| 2,707,965 | 5/1955 | Allen . |
| 2,867,213 * | 1/1959 | Thomas, Jr. .......................... 604/247 |
| 3,417,750 | 12/1968 | Carson . |
| 3,463,159 | 8/1969 | Heimlich . |
| 3,570,525 | 3/1971 | Borsum et al. . |
| 3,572,375 * | 3/1971 | Rosenberg ........................... 604/247 |
| 3,626,980 | 12/1971 | Svensson . |
| 4,081,176 | 3/1978 | Johnson . |
| 4,083,115 * | 4/1978 | McKelvey ............................... 433/96 |
| 4,160,383 * | 7/1979 | Rauschenberger .................... 604/247 |
| 4,232,677 | 11/1980 | Leibinsohn . |
| 4,286,622 | 9/1981 | Ninomiya et al. . |
| 4,474,209 | 10/1984 | Akhtarekhavari . |
| 4,735,607 | 4/1988 | Keith, Jr. . |
| 4,758,224 | 7/1988 | Siposs . |
| 4,904,236 | 2/1990 | Redmond et al. . |
| 4,966,551 | 10/1990 | Betush . |
| 4,998,880 * | 3/1991 | Nerli ..................................... 433/80 |
| 5,044,953 * | 9/1991 | Sullivan ................................ 433/92 |
| 5,144,342 * | 5/1992 | Young et al. ......................... 433/95 |
| 5,158,539 | 10/1992 | Kolff et al. . |
| 5,165,891 | 11/1992 | Young et al. . |
| 5,267,586 | 12/1993 | Jankavaara . |
| 5,295,830 | 3/1994 | Shen et al. . |
| 5,425,637 * | 6/1995 | Whitehouse et al. .................. 433/95 |
| 5,441,410 | 8/1995 | Segerdal . |
| 5,464,350 | 11/1995 | Bierbaum . |
| 5,464,397 * | 11/1995 | Powers, Jr. ........................... 604/246 |
| 5,509,802 | 4/1996 | Whitehouse et al. . |
| 5,520,041 | 5/1996 | Haswell . |
| 5,535,785 | 7/1996 | Werge et al. . |
| 5,725,374 * | 3/1998 | Young ................................... 433/95 |
| 5,855,478 * | 1/1999 | Van ....................................... 433/95 |

* cited by examiner

*Primary Examiner*—Ralph A. Lewis
(74) *Attorney, Agent, or Firm*—Dicke, Billig & Czaja, P.A.

(57) ABSTRACT

A dental apparatus backflow-prevention system substantially prevents contaminant backflow into a patient's mouth. The system includes a saliva ejector tube for insertion into the patient's mouth and for removal of saliva, blood, etc. when a vacuum is applied. A backflow-prevention device receives fluid from the saliva ejector tube and includes an internal valve seat. Valve componentry disposed within the backflow-prevention device includes a housing and a seating mechanism operably supported by the housing to automatically engage the valve seat and prevent contaminant backflow upon release of the vacuum. Upon application of vacuum, however, the seating mechanism automatically disengages from the valve seat and allows fluid flow away from the patient's mouth. According to one embodiment, the seating mechanism is functionally flexible for movement within the housing away from the valve seat, and is biased to move toward the valve seat upon release of vacuum. Corresponding methods provide similar advantages.

29 Claims, 19 Drawing Sheets

BACKFLOW PREVENTION SYSTEM IN SUCTIONING APPARATUS

CROSS-REFERENCE TO RELATED APPLICATIONS

This application is a Continuation-In-Part of U.S. application No. 08/867,752, filed Jun. 3, 1997, now abandoned which claims priority under 35 U.S.C. §119(e) to U.S. Provisional application No. 60/019,090, filed Jun. 3, 1996, both of which applications are incorporated herein by reference.

BACKGROUND OF THE INVENTION

1. Field of the Invention

The invention relates to suctioning devices, and more particularly to medical suctioning devices that are adapted to prevent backflow of saliva, blood and other contaminants into the mouth of a dental patient, for example. Embodiments of the invention have potential application beyond the dental and medical arts, however.

2. Description of Related Art

It has been recognized in the art that cross-contamination between patients, for example, dental patients, can occur when suctioning devices attached to vacuum lines are used to remove various bodily and/or externally introduced fluids. Although the disposable distal ends of these devices typically are changed between patients, the vacuum lines employed typically are not changed. Saliva, blood and other contaminants pass from the distal end into the vacuum line, where they can remain until arrival of the next patient. When a new distal end is inserted onto the vacuum line for a new patient, contaminants from the previous patient can backflow from the vacuum line into the distal end and enter the patient's mouth, for example. Clearly, with the growing incidence of AIDS and other communicable diseases, this is a situation to be avoided.

A number of prior art devices have attempted to prevent backflow and the resulting likelihood of cross-contamination between patients. U.S. Pat. Nos. 5,425,637 and 5,509,802 to Whitehouse, et al. and 5,464,397 to Powers, Jr., which are incorporated herein by reference, disclose prior art attempts to prevent or at least minimize contaminant backflow and cross-contamination. The two Whitehouse patents disclose suction lines having vacuum-release apertures through a tubular sidewall of a saliva ejector tip. If a patient closes his or her lips around the tip, the vacuum-release aperture is said to prevent creation of a temporary high vacuum in the patient's mouth; the aperture also likely prevents stoppage of air and/or fluid, at least between the aperture and the rest of the system. The Powers, Jr. patent, on the other hand, appears to rely merely on a "tortuous path" within the device to substantially prevent backflow of bacteria.

However, as recent studies are believed to have shown, a boundary layer can form around the internal circumference of many currently used suctioning devices. The boundary layer is the portion of air and/or other fluid flowing in the immediate vicinity of the internal circumference. Flow within the boundary layer is severely reduced, even eliminated due to the forces of adhesion and viscosity caused by the internal circumference. Because suction within the boundary layer is reduced or eliminated, a "bio-film" can be created, allowing saliva, blood and other contaminants to flow by gravity, for example, from the main vacuum system of a dental office, through saliva ejector assemblies and into the mouths of patients.

It is not believed that prior art suctioning devices adequately account for or address backflow caused by boundary layer conditions, and/or other conditions such as mouth-induced backflow suction. Prior art devices thus allow an unacceptably high likelihood of cross-contamination between patients. Clearly, a need has arisen for a solution to this problem.

SUMMARY OF THE INVENTION

To address the above and other problems, a dental apparatus backflow-prevention system substantially prevents contaminant backflow into a patient's mouth. The system includes a saliva ejector tube for insertion into the patient's mouth and for removal of saliva, blood, etc. when a vacuum is applied. A backflow-prevention device receives fluid from the saliva ejector tube and includes an internal valve seat. Valve componentry disposed within the backflow-prevention device includes a housing and a seating mechanism operably supported by the housing to automatically engage the valve seat and prevent contaminant backflow upon release of the vacuum. Upon application of vacuum, however, the seating mechanism automatically disengages from the valve seat and allows fluid flow away from the patient's mouth. According to one embodiment, the seating mechanism is functionally flexible for movement within the housing away from the valve seat, and/or is spring-biased to move toward the valve seat upon release of vacuum. Corresponding devices and methods provide similar advantages.

BRIEF DESCRIPTION OF THE DRAWINGS

Embodiments of the invention will be described with respect to the Figures, in which like numerals denote like or similar elements and in which.

DETAILED DESCRIPTION OF PREFERRED EMBODIMENTS

Embodiments of the invention have wide application to a number of medical procedures and environments. Suction is often used in dental applications, as described above. Suctioning devices are also typically used to drain fluid and remove blood from many surgical environments, aid in respiration, and aid in a number of other medical and surgical procedures. Additionally, suctioning devices in which cross-contamination is undesirable also are used in non-medical and non-surgical environments. Therefore, although preferred embodiments of the invention will be described with respect to dental devices and applications, the invention is not limited to these embodiments.

Figure 1:
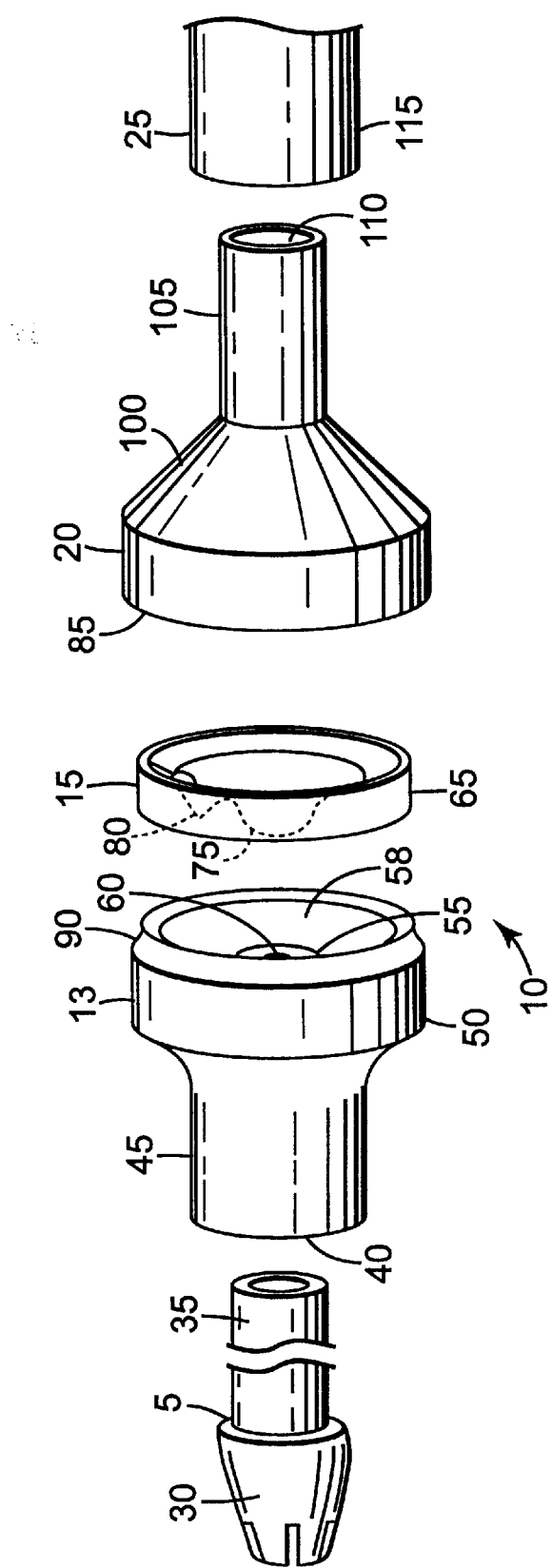
FIG. 1 is an isometric, exploded view of a dental suction system according to an embodiment of the invention.
Figure 2:
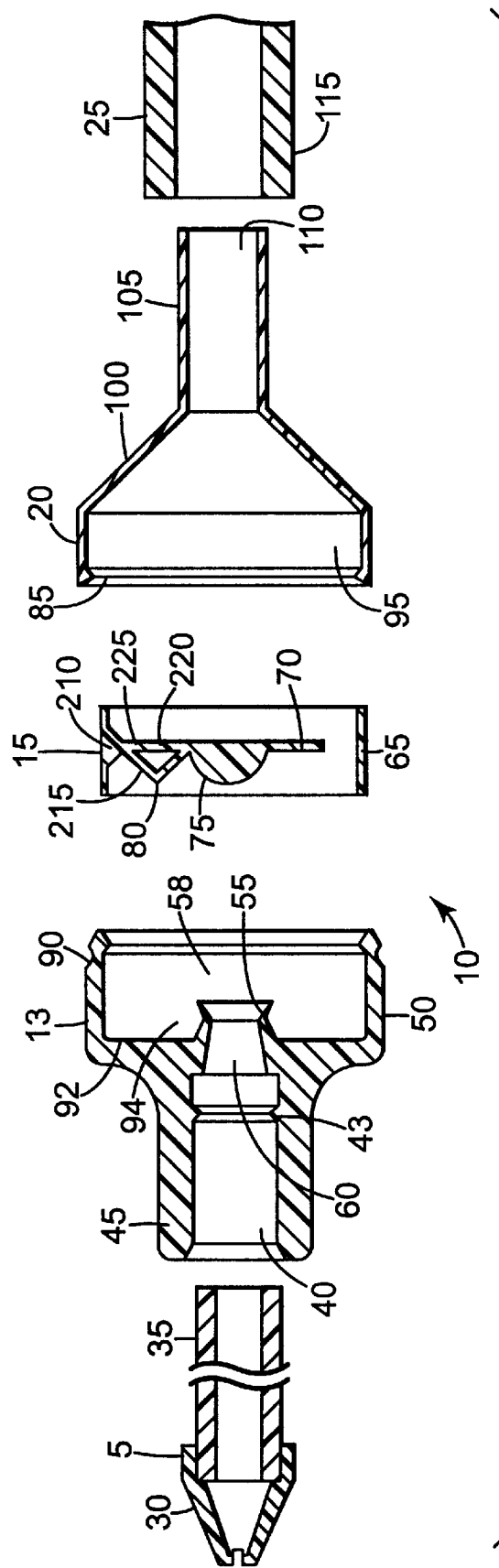
FIG. 2 is a cross-sectional view of the FIG. 1 system.

As shown in e.g. FIGS. 1 and 2, a dental suctioning device according to the invention preferably includes saliva ejector tube 5, also called a dental ejector tip, for insertion into a patient's mouth, backflow-prevention device 10 with corresponding distal portion 13, internal valve componentry 15, and main body cap or proximal portion 20, and vacuum source/apparatus 25. As shown in FIG. 1, vacuum source/apparatus can comprise a vacuum tube. Together, saliva ejector tube 5 and backflow-prevention device 10, optionally further including vacuum source/apparatus 25, make up a backflow-prevention system, also called a dental suction system, according to an embodiment of the invention.

Saliva ejector tube 5 includes distal end 30, which preferably serves as a mouthpiece for contacting and directly withdrawing saliva, blood and/or other fluids and contaminants from a patient's mouth during a dental procedure, for example. Saliva ejector tube 5 further includes proximal end 35, for connection to backflow-prevention device 10. Specifically, proximal end 35 of saliva ejector tube 5 is preferably received within substantially straight-walled orifice 40 of neck portion 45 in distal portion 13 of backflow-prevention device 10. Orifice 40 allows fluids to enter main body 50 of backflow-prevention device 10. According to the illustrated embodiment, orifice 40 includes a portion 43 of reduced circumference, to "bite" into and thus better secure ejector tube 5. Of course, other connection arrangements between tube 5 and connection device 10 are contemplated according to the invention.

Backflow-prevention device 10 also includes blocking seat 55 comprising a central orifice, as shown. Blocking seat 55 preferably is directly connected to central cavity 60, which receives fluids from orifice 40 and which preferably is of a substantially tapered shape, as shown, to improve flow characteristics. Blocking seat 55 is disposed distally of substantially annular orifice 58, described below. According to one embodiment, seat 55 is of substantially thin-walled and/or flexible construction, to better conform to the shape of an engagement member of associated valve componentry, as will be described.

Valve componentry 15, supported within a valve chamber defined by distal and proximal portions 13, 20 according to an embodiment of the invention, will now be described with respect to FIGS. 1, 2 and 11. Valve componentry 15, supported within a valve chamber defined by distal and proximal portions 13, 20, includes outer support ring or housing 65, which according to the illustrated embodiment is substantially circular but can take other shapes as may be desirable to match the internal or external shapes of distal and proximal portions 13, 20 of backflow-prevention device 10. Outer ring 65 supports seating mechanism or blocking member 70, which allows fluid flow of saliva and/or other substances when vacuum is applied via vacuum source 25, and substantially prevents backflow of such substances when vacuum is not applied by seating within seat 55.

Figure 11:
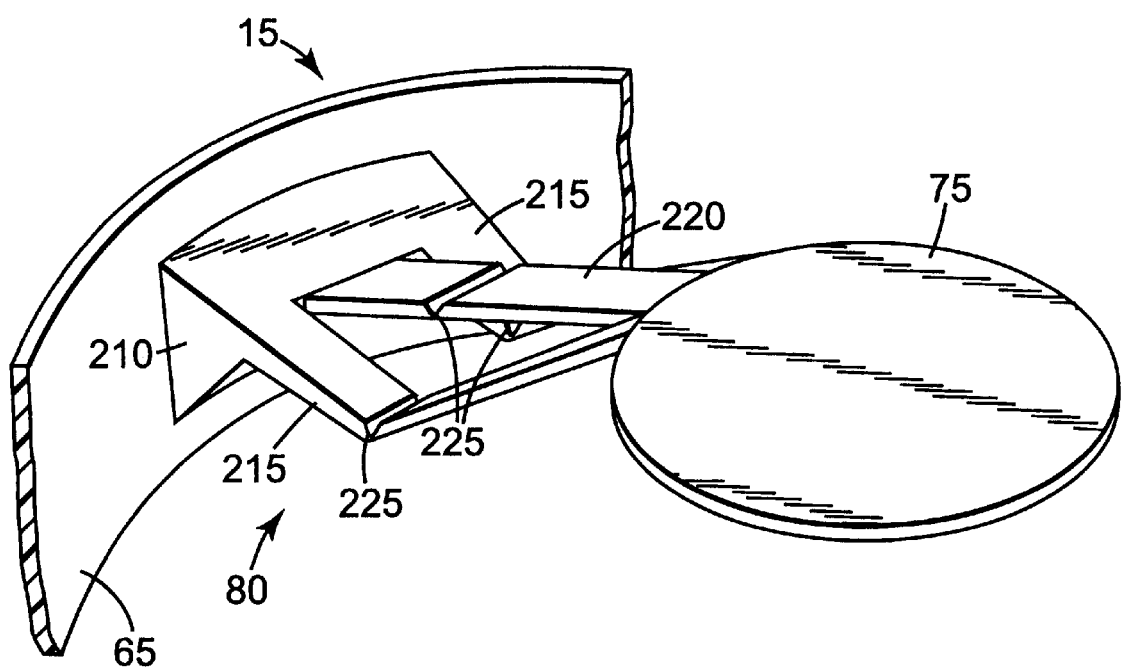
FIG. 11 is an isometric view of valve componentry according to the embodiment of FIGS. 1 and 2.

Seating mechanism 70 includes engagement member 75, preferably of substantially ball-like or bulbous shape, and biasing member or spring assembly 80, best shown in FIG. 11. According to the illustrated embodiment, spring assembly 80 comprises a substantially triangular base portion 210, supporting two outer legs 215 and a central leg 220. Legs 215, 220 each include notches 225, the placement of which can be chosen to affect the spring action of seating mechanism 70, i.e., the force necessary to open and/or close the orifice in seat 55. Although only one notch is disposed in each leg 215, 220 in the illustrated embodiments, it is contemplated that each leg could have a plurality of notches 225.

According to a preferred embodiment, spring assembly 80 is in a minimal-stress condition when engagement member 75 is engaged with seat 55. A minimal-stress condition is preferred over a zero-stress condition, to minimize the tendency of engagement member 75 to bounce or otherwise move in seat 55. Thus, in the absence of external forces, the orifice of seat 55 is closed and backflow is substantially prevented. After vacuum is turned on and reaches a certain pressure, however, legs 215, 220 bend such that engagement member 75 moves into an open position with respect to seat 55, allowing fluid to flow from the patient's mouth toward vacuum apparatus 25. As is clear from the figures, housing 65 is constructed such that the vacuum source draws fluid within housing 65 only from left to right as viewed in FIG. 2, i.e., from the inlet of housing 65 to the outlet of housing 65. As vacuum is shut off, seating mechanism 70 snaps or otherwise moves to a closed position. Seating mechanism 70 thus is functionally flexible.

Of course, a variety of connection arrangements between seating mechanism 70 and the inside surface of outer ring 65 are contemplated. For example, engagement member 75 can be connected to outer ring 65 by a plurality of circumferentially spaced spring assemblies 80 to allow e.g., substantially linear movement of seating engagement member 75 into and out of engagement with blocking seat 55 of backflow-prevention device 10. Engagement member 75 also can include a substantially cup-shaped or other surface for close interface with housing 65, such that any backflow helps move seating mechanism 70 to its closed position.

Returning primarily to FIGS. 1 and 2, main body cap 20 preferably includes annular flange 85 for connection to the rest of backflow-prevention device 10, for example by snap-fitting into snap-ring 90 thereof. Because the distal and proximal portions 13, 20 of backflow-prevention device 10 are constructed to snap-fit together, it may be beneficial in certain situations (e.g., production environments) for valve componentry 15 to be readily removably disposed within backflow-prevention device 10 for easy replacement, if needed. In most applications, however, backflow-prevention device 10 is intended to be disposable in its entirety and therefore replacement of componentry likely will not be needed.

Valve componentry 15 is accommodated within annular orifice 58 of distal portion 13 preferably by a friction fit, with substantially triangular members 93 "biting" into housing 65 of componentry 15 as it is inserted into recess 58. Proximal portion 20 includes similar members for better engaging snap-ring 90, and for additionally compressing valve componentry 15.

It should also be noted that seat 55 extends a sufficient distance above the distal walls 92 of orifice 58 to create a "damming" effect for reducing backflow past seat 55. Before backflow can reach seat 55, it must build up within well 94 surrounding seat 55 and reach a "height" sufficient to flow through the orifice in seat 55. This creates a time delay, giving seating mechanism 70 time to close before backflow can occur.

Main body cap 20 also preferably includes substantially straight-walled cavity 95 and substantially tapered portion 100, which leads to neck portion 105. Neck portion 105 includes orifice 110 for connection to receptacle portion 115 of vacuum apparatus 25. Fluids pass through orifice 110 into receptacle portion 115 for removal, and are prevented from flowing back toward saliva ejector tube 5 by valve componentry 15 and associated housing. Vacuum apparatus 25 also preferably includes an on/off valve to activate/deactivate vacuum pressure.

Figure 12:
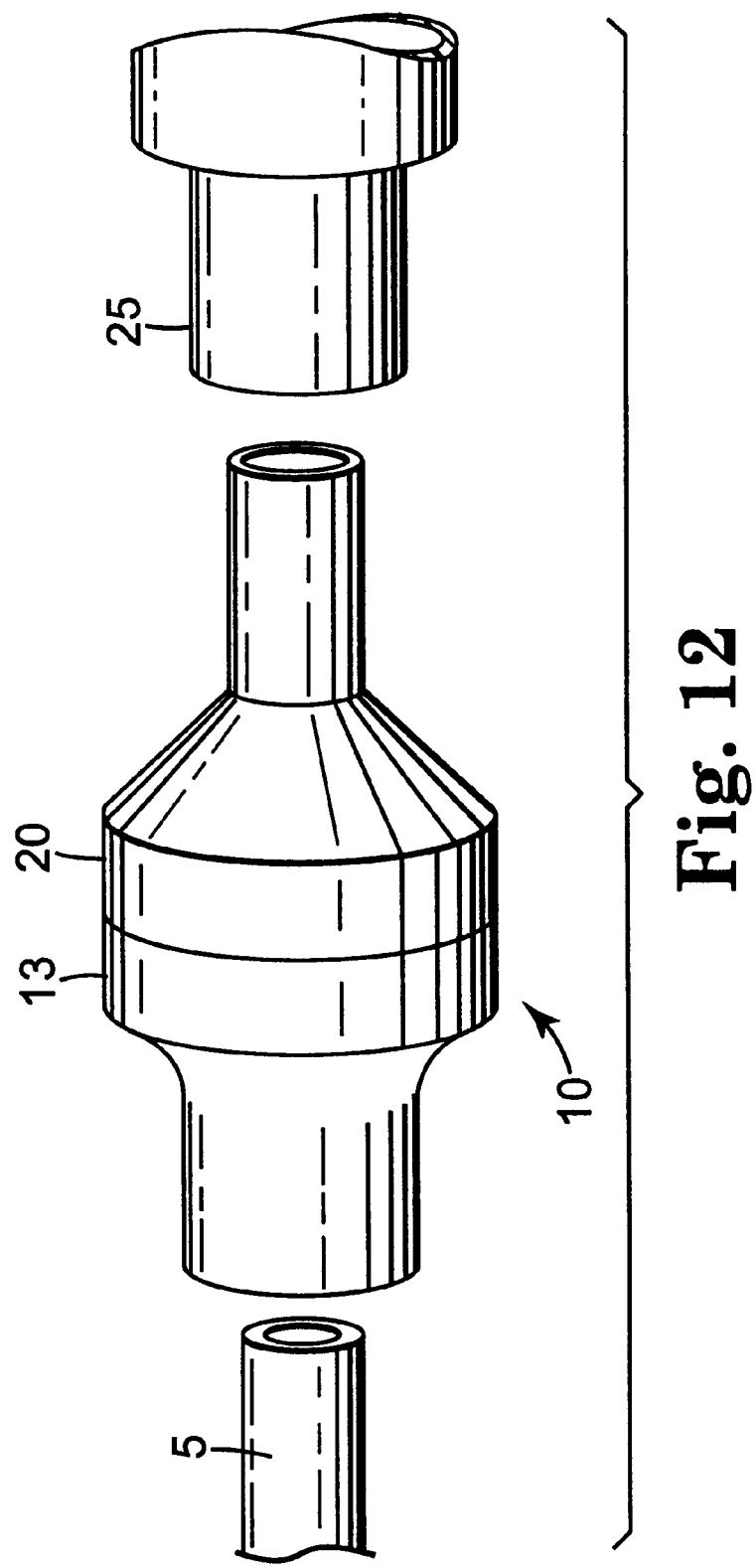
FIG. 12 is an isometric view showing the embodiment of FIGS. 1 and 2 in assembled form.

FIG. 12 shows the system of FIGS. 1 and 2 in an assembled condition.

Figure 3:
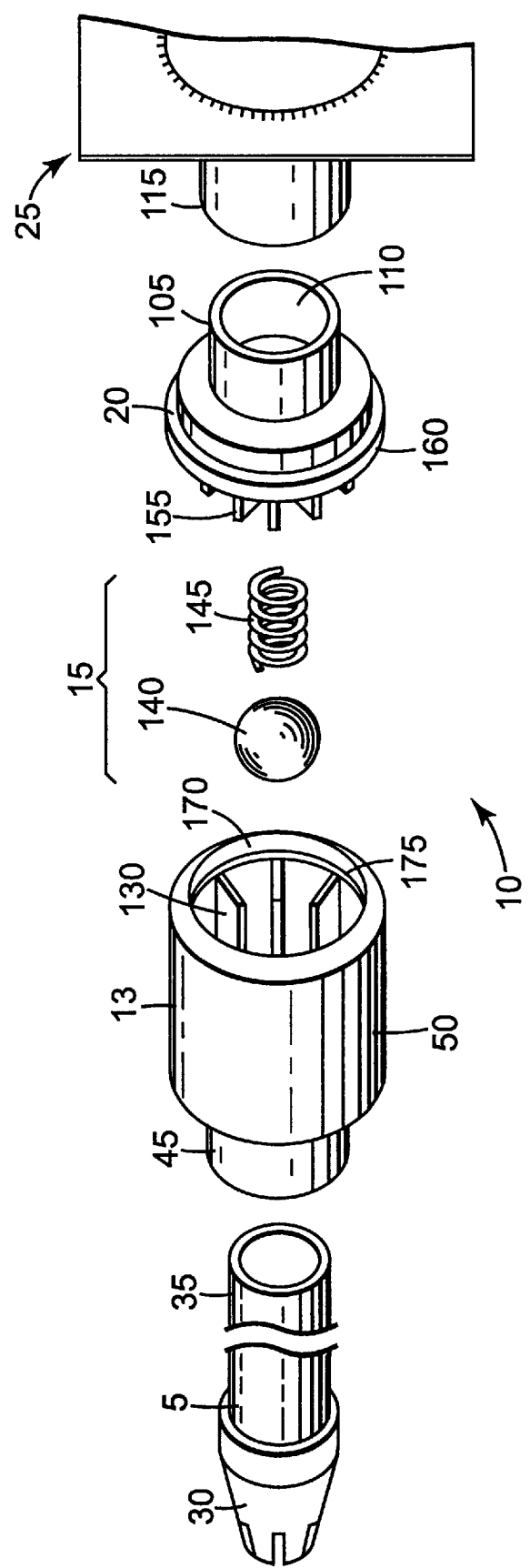
FIG. 3 is an isometric, exploded view of a dental suction system according to an alternative embodiment of the invention.
Figure 4:
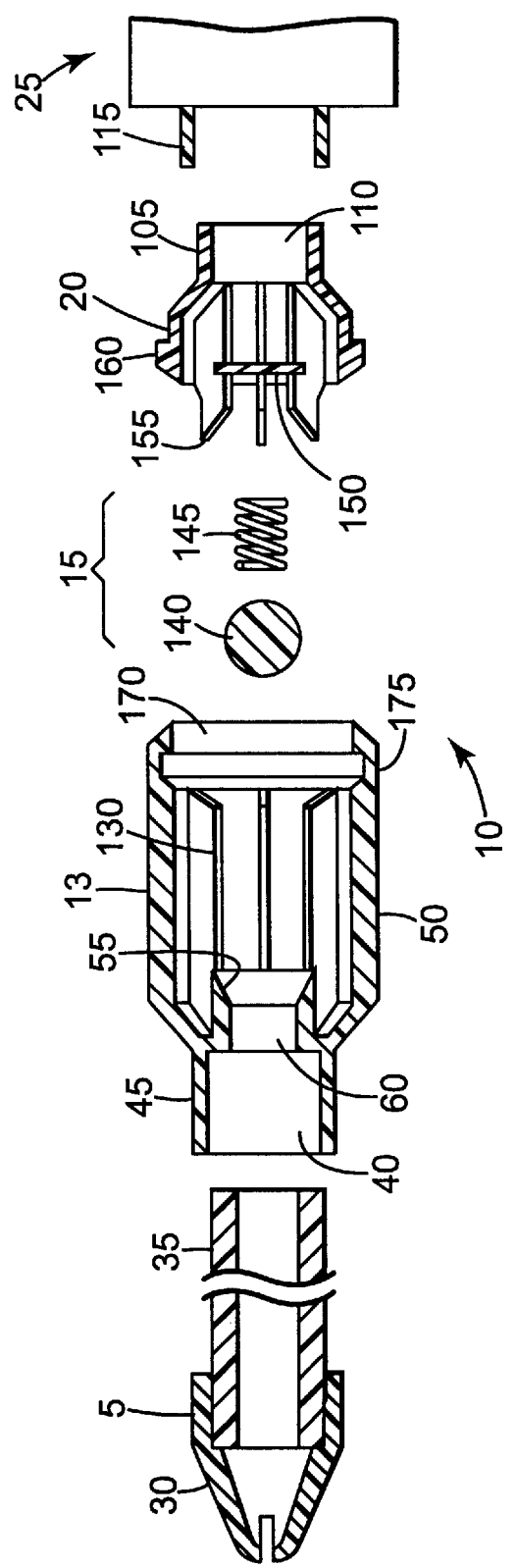
FIG. 4 is a cross-sectional view of the FIG. 3 system.
Figure 5:
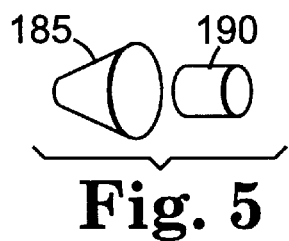
FIG. 5 is an isometric view of alternative valve componentry according to an embodiment of the invention.
Figure 6:
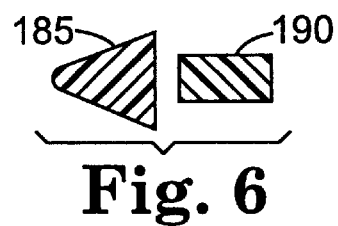
FIG. 6 is a cross-sectional view of the FIG. 5 componentry.
Figure 7:
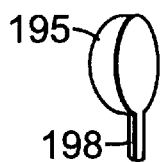
FIG. 7 is an isometric view of alternative valve componentry according to an embodiment of the invention.
Figure 8:
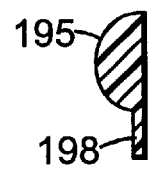
FIG. 8 is a cross-sectional view of the FIG. 7 componentry.
Figure 9:
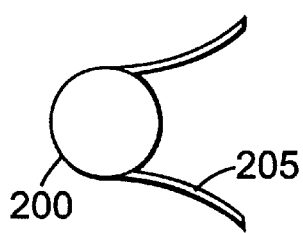
FIG. 9 is an isometric view of alternative valve componentry according to an embodiment of the invention.
Figure 10:
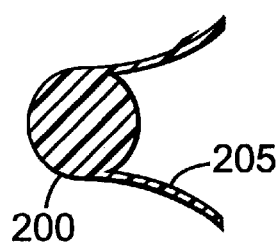
FIG. 10 is a cross-sectional view of the FIG. 9 componentry.

FIGS. 3 and 4 illustrate an alternative embodiment of the invention. According to this embodiment, saliva ejector tube 5 is substantially similar to that described in the previous embodiment. Backflow-prevention device 10, however, includes a plurality of internal fins 130, which lead to blocking seat 55. Although six fins 130 are used according to the illustrated embodiment, a greater or lesser number can be used as desired.

Valve componentry 15 according to this embodiment includes preferably spherical ball 140, urged toward blocking seat 55 by wound spring 145. When vacuum is not applied, ball 140 is substantially sealingly engaged with seat 55, and componentry 15 thus prevents backflow into saliva ejector tube 5. When vacuum is applied, on the other hand, ball 140 compresses spring 145 against seat 150 of main body cap 20, allowing fluid to flow from saliva ejector tube 5 through backflow-prevention device 10 and into vacuum apparatus 25. As with the embodiment of FIGS. 1 and 2, the housing surrounding valve componentry 15 is constructed such that the vacuum source draws fluid within the housing only from its inlet to its outlet.

Main body cap 20 according to the embodiment of FIGS. 3 and 4 also includes a plurality of fins 155 preferably corresponding to fins 130 of the rest of backflow-prevention device 10. Together fins 130, 155 control movement of valve componentry 15 and allow flow of fluid around componentry 15 through main body portion 20 when vacuum is applied. Fins 130, 155 also substantially prevent relative rotation between backflow-prevention device 10 and main body cap 20.

As illustrated, main body cap 20 also preferably includes annular flange 160 for entering orifice 170 of backflow-prevention device 10 and snap-fitting into corresponding annular recess 175 therein. Other elements of the embodiment illustrated in FIGS. 3 and 4 are similar to those described with respect to FIGS. 1 and 2, and will not be described again, to simplify the disclosure.

Valve componentry 15 can take various alternative forms, as shown in FIGS. 5–8. Conical device 185, for example, can be the engagement member and used in connection with resilient material 190 to maintain pressure on blocking seat 55 in the absence of vacuum and thus prevent backflow. Alternatively, flap-device engagement member 195 with at least one seating flange or lever arm 198 can be used, as can blocking portion 200 with spring-actuating portions 205. As shown in, e.g., FIGS. 7 and 8, lever arm 198 can be one piece with flap device 195.

Preferably, valve componentry 15 is of very light weight to ensure a wide enough opening at blocking seat 55 when vacuum is applied. Valve componentry 15 allows the orifice within blocking seat 55 to be relatively large, greatly reducing the likelihood of clogging. Further, saliva ejector tube 5 and backflow-prevention device 10, which together may be called a dental ejector tip, are preferably disposable according to an embodiment of the invention.

Figure 13:
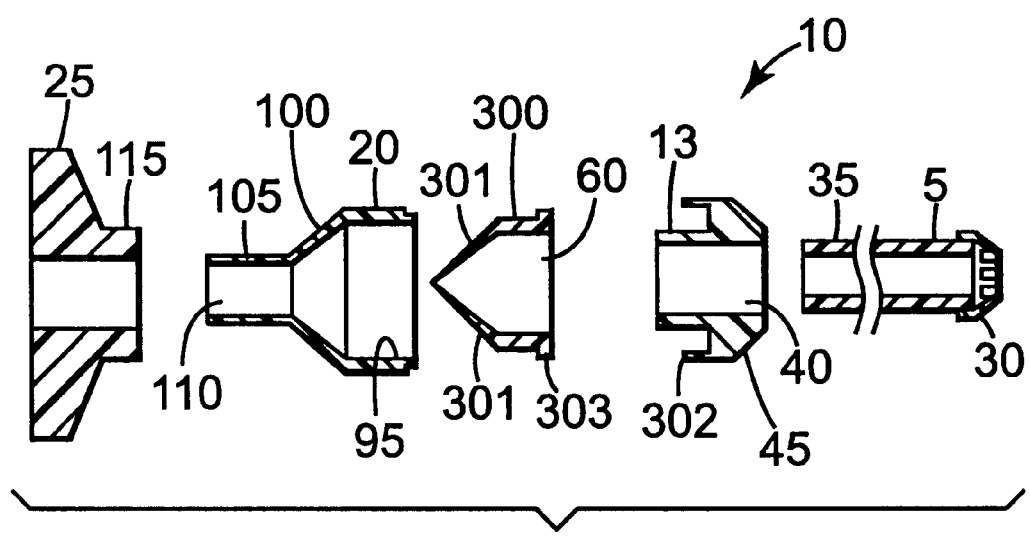
FIG. 13 is a cross-sectional, exploded view of a dental suction system according to an alternative embodiment of the invention.
Figure 13A:
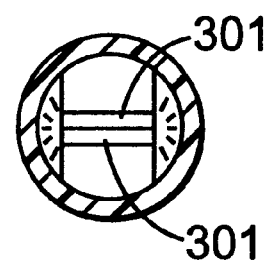
FIG. 13A is a front cross-sectional view of a portion of the FIG. 13 system.

Another embodiment of the invention is shown in FIG. 13. The dental suctioning device includes saliva ejector tube 5 for insertion into a patient's mouth, backflow prevention device 10 with corresponding distal portion 13, elastic valve 300, main body cap 20, and vacuum source/apparatus 25. Elastic valve 300 is available, for completely different commercial uses, from Vernay Laboratories, Inc. Ejector tip 5 includes distal end 30 and hollow tube with proximal end 35. Distal portion 13 of backflow prevention device 10 comprises neck portion 45, tabs 302, and bore or orifice 40. Elastic valve 300 comprises flange 303, sloping portions 301, and internal cavity 60. As shown in the front view of FIG. 13A, sloping portions 301 are normally closed and form a generally straight line where they come together. Main body cap 20 comprises tapered portion 100, neck portion 105, bore or orifice 110, and straight wall portion 95. Vacuum source 25 comprises receptacle portion 115.

In this embodiment, proximal end 35 of ejector tip 5 is received by neck portion 45 of distal portion 13. Tabs 302 of distal portion 13 receive flange 303 of elastic valve 300. Elastic valve 300 is received by straight wall portion 95 of main body cap 20. Neck portion 105 of main body cap 20 is received by receptacle portion 115 of vacuum source 25.

In operation, opposed sloping portions 301 of elastic valve 300 are biased toward each other and closed when the system is at or between negative and low vacuum pressure, to prevent backflow such that air and fluids do not flow from the main waste system back into tip 5 and back into the patient's mouth. When the system is under normal vacuum pressure (e.g. between 8 and 27 PSI vacuum), however, sloping portions 301 are deflected, i.e. they flare outwardly, such that through-flow is established. Such through-flow occurs along a central longitudinal axis of backflow prevention device 10.

Figure 14:
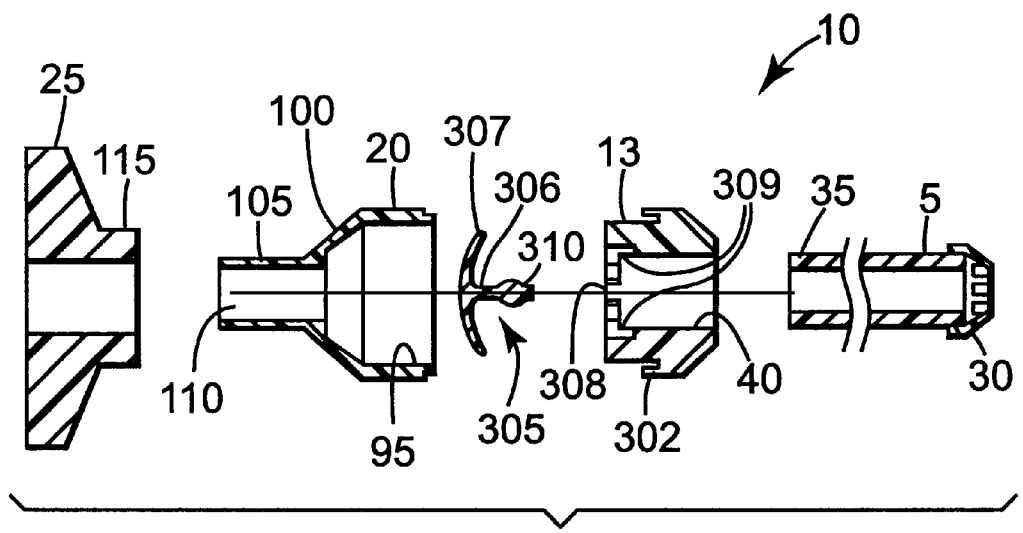
FIG. 14 is a cross-sectional, exploded view of a dental suction system according to an alternative embodiment of the invention.
Figure 15:
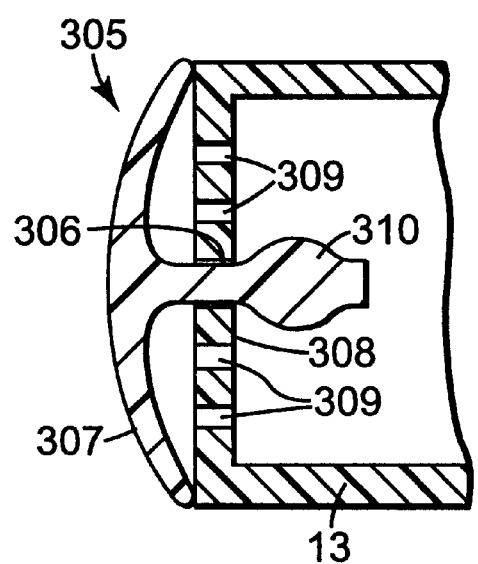
FIG. 15 is an enlarged, cross-sectional view of a portion of the dental suction system shown in FIG. 14.

FIGS. 14 and 15 show alternative embodiments of the invention. With these embodiments, the valve function is performed by elastic circular flap 305, which comprises flap portion 307, neck 306 connected to flap portion 305 at a central area thereof, and bulge portion 310. Flap portion 305 is available, for completely different commercial uses, from Vernay Laboratories, Inc. Also, in this embodiment, distal portion 13 comprises aperture 308 and openings 309. Elastic circular flap 305 is disposed within distal portion 13 of backflow prevention device 10 so that neck 306 is within aperture 308, bulge portion 310 is inside distal portion 13, and flap portion 307 is disposed outside of distal portion 13.

When the system is under normal operating vacuum pressures, typically between 12 and 27 PSI vacuum, flap portion 307 bends and flares in the direction of fluid flow to allow fluid to pass through openings 309. But at low or negative vacuum pressure, flap portion 307 seals against the surface of distal portion 13 and blocks backflow by covering openings 309.

According to one method of manufacture for this embodiment, bulge portion 310 is pulled through aperture 308. Once bulge portion 310 passes through aperture 308, it expands to prevent withdrawal. Flap portion 307 preferably is held in tension against the face of distal portion 13.

According to other embodiments of the invention, FIGS. 16–19 show biased arm and sealing flap combinations. With these embodiments, sealing flap 322 is connected to main body cap 20 by biased arm 323. Distal portion 13 of backflow prevention device 10 comprises sloped ledger 320 which, when fit into main body cap 20, pushes against biased arm 323. In operation, sealing flap 322 seals against bore or orifice 40 in the absence of sufficient vacuum pressure, so that backflow is prevented. But, under normal operating vacuum pressures, biased arm 323 bends to allow sealing flap 322 to unseal from orifice 40 so that air and fluids may pass through the valve.

Ledger 320 preferably is an insert ledger that pushes against biased arm 323 during assembly and makes the initial lift of the biased arm when assembled. Ledger 320 also may extend beyond biased arm 323 after assembly, e.g. by using a friction fit to lift the arm 323 and then slip past it, allowing arm 323 to operate freely in a larger zoned area in the ledger.

Figure 16:
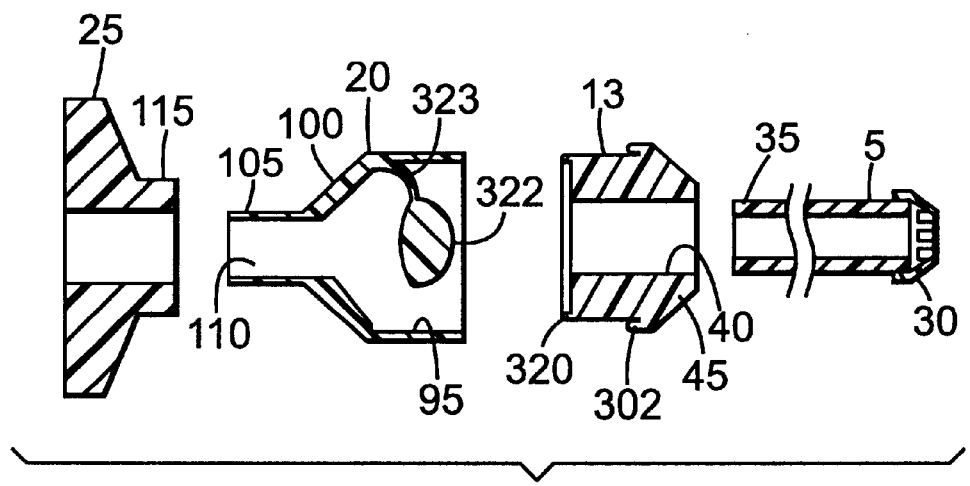
FIG. 16 is a cross-sectional, exploded view of a dental suction system according to an alternative embodiment of the invention.
Figure 16A:
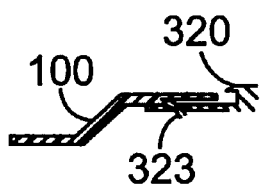
FIGS. 16A–B are cross-sectional views of portions of the FIG. 16 system.
Figure 16B:
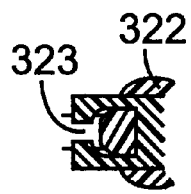
Figure 17:
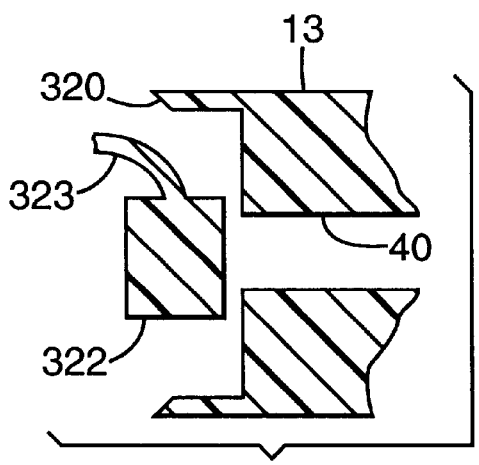
FIG. 17 is an enlarged, cross-sectional view of an alternative embodiment.
Figure 18:
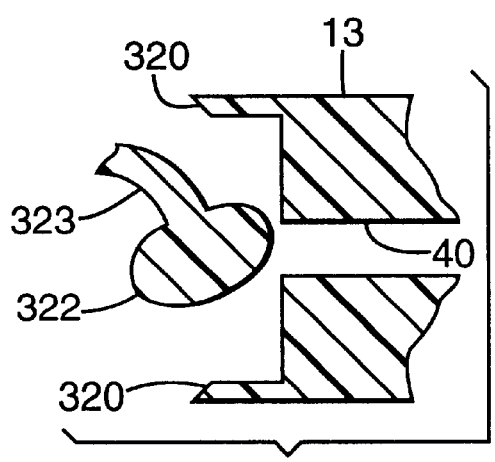
FIG. 18 is an enlarged, cross-sectional view of an alternative embodiment.
Figure 19:
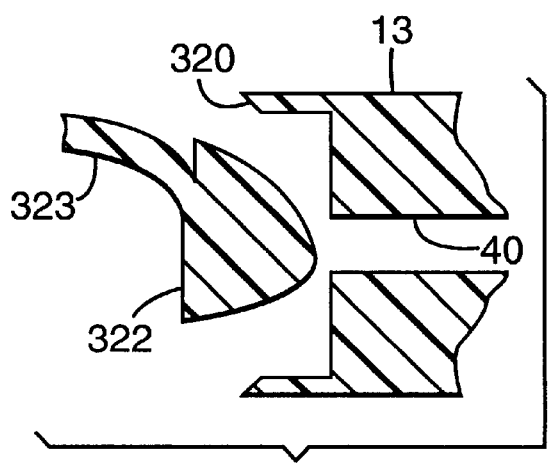
FIG. 19 is an enlarged, cross-sectional view of an alternative embodiment.

As shown in FIGS. 16A–16B, arm 323 slips past a friction fit in the edges of ledger 320 and resides in a slot with room for arm 323 to move up and down. The slot is of a particular shape, as illustrated, extending from ledger 320 on the inside of tapered portion 100 of proximal portion 20. As the slot slides against the inside of tapered portion 100, it lifts arm 323 until arm 323 slips through the slot and rests in the open area.

Biased arm 323 may be made of material that provides an inherent bias to the arm, to create the force that causes sealing flap 322 to make a seal. Sealing flap 322 may be made in a variety of shapes, as shown in FIGS. 16–19, such as a flat sealing face (FIG. 17), a spherical sealing flap (FIG. 18), a conical shape (FIG. 19), or other shapes that will be readily apparent to those skilled in the art after reading this application.

Figure 20:
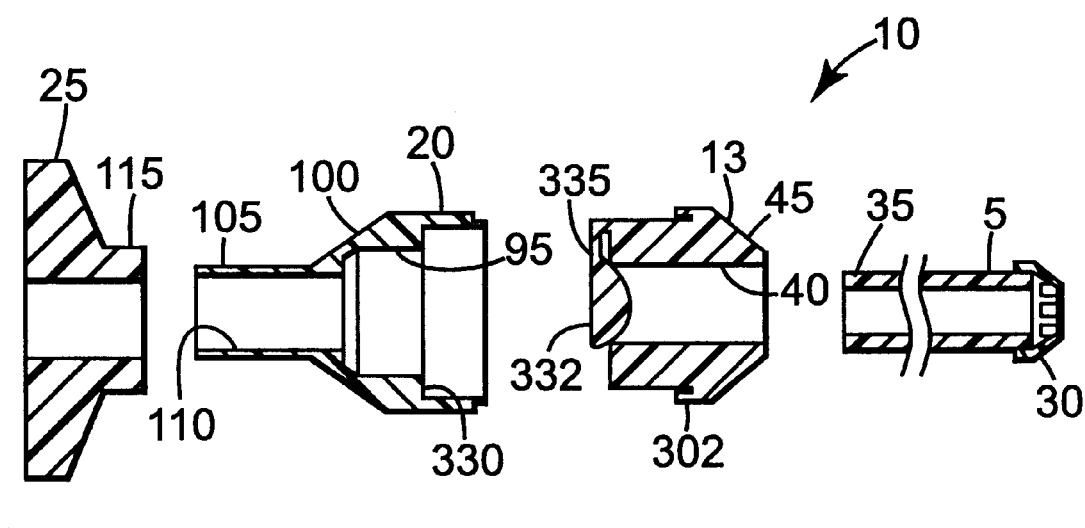
FIG. 20 is a cross-sectional, exploded view of a dental suction system according to an alternative embodiment of the invention.

According to the FIG. 20 embodiment, sealing flap 332 is connected by biased arm 335 to the wall of distal portion 13. Main body cap 20 comprises internal ledger 330. After assembly, ledger 330 pushes against biased arm 335 at a point on arm 335 that creates a biasing force to keep sealing flap 332 in the closed position. In operation, the biasing force on biased arm 335 created by ledger 330 holds sealing flap 332 in the sealed position at negative and low vacuum pressures. Under normal operating vacuum pressure, biased arm 335 bends, allowing sealing flap 332 to move so that fluids may flow through the valve apparatus. Sealing flap 332 may be flat, conical, spherical, or have other shapes as disclosed elsewhere in this application.

Figure 21:
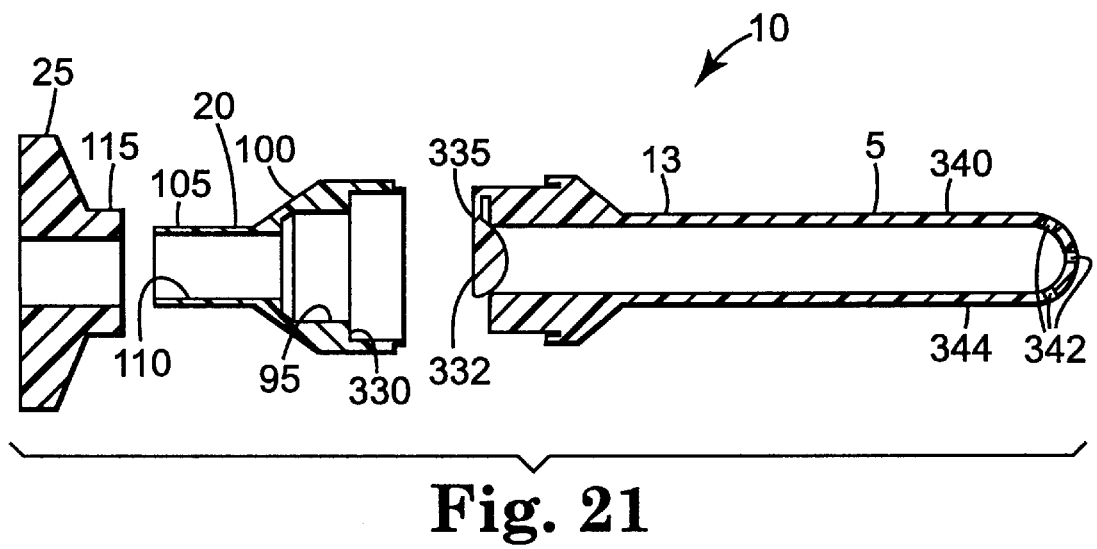
FIG. 21 is a cross-sectional, exploded view of a dental suction system according to an alternative embodiment of the invention.

According to the FIG. 21 embodiment, ejector tip 5 and distal portion 13 are made as a single component. Distal portion 13 comprises a valve apparatus such as that previously shown in FIG. 16 or one of the other embodiments, for example. Ejector tip 5 comprises projected tube 340 with tube end 344 defining one or more holes 342. Holes 342 allow for air and fluids and other materials to enter the tube from the patient's mouth.

Figure 22:
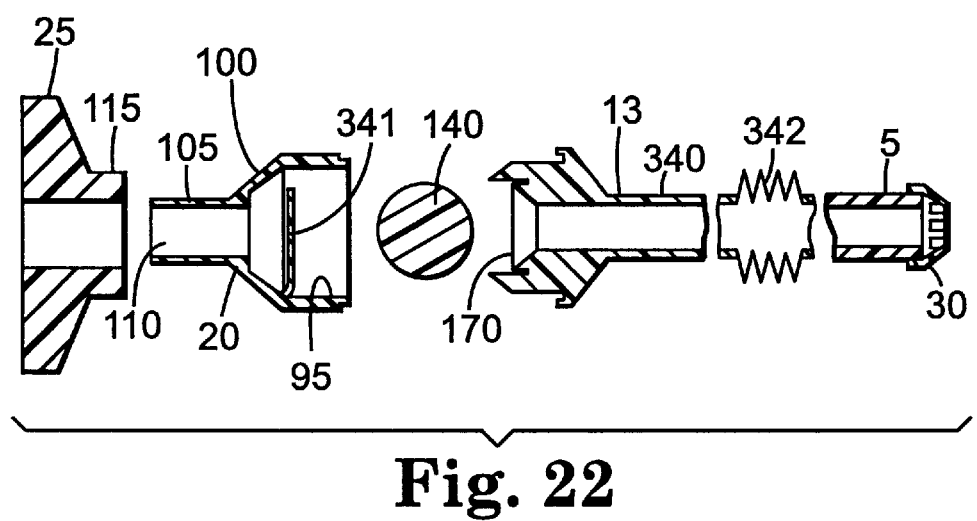
FIG. 22 is a cross-sectional, exploded view of a dental suction system according to an alternative embodiment of the invention.

As shown in FIG. 22, ejector tip 5 or projected tube 340 thereof may comprise corrugated walls 342. Walls 342 may be used in combination with other embodiments, e.g. those shown in FIGS. 3, 4, and 11, among others. FIG. 22 also shows alternative biasing member 341, for urging ball 140 into a sealing position. Corrugated walls 342 are flexible and bendable so that projected tube 340 may be stretched, compressed, bent, or otherwise manipulated while the dental suction system is in use. The corrugated walls may be configured so that they retain their shape after being bent, elastically return to their original shape after being bent, or with properties between these two extremes.

Figure 23:
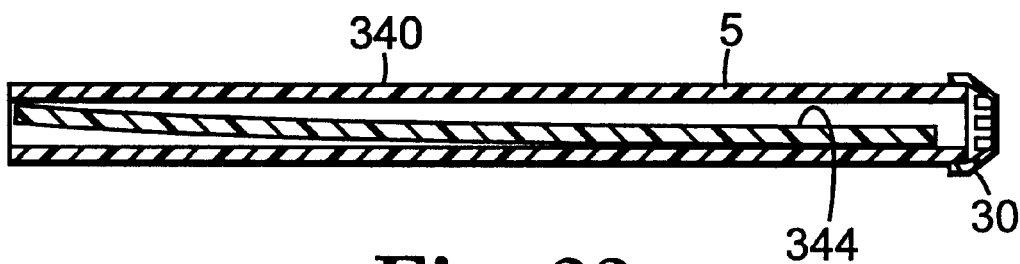
FIG. 23 is a cross-sectional view of a dental suction system according to an alternative embodiment of the invention.
Figure 24:
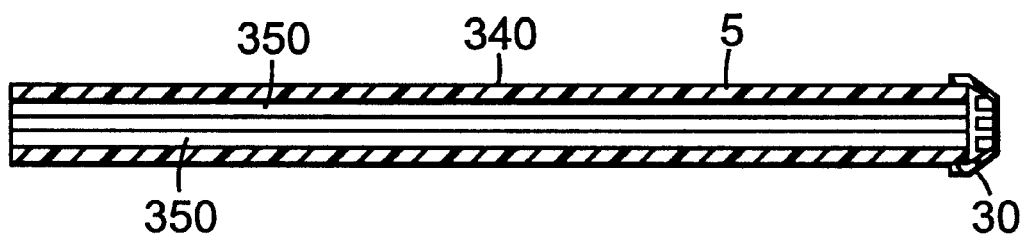
FIG. 24 is a cross-sectional view of a dental suction system according to an alternative embodiment of the invention.
Figure 25:
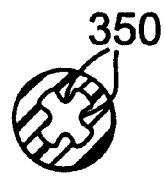
FIG. 25 is an end view of the FIG. 24 embodiment.

As shown in FIG. 23, rod 344 may be inserted within projected tube 340. Rod 344 is made of bendable material that will retain its shape after being manipulated to a desired position by the user, according to this embodiment. Alternatively, as shown in FIGS. 24–25, projected tube 340 may be manufactured to incorporate ribs 350, running lengthwise along tube 340, that cause tube 340 to retain its shape after manipulation.

Figure 26:
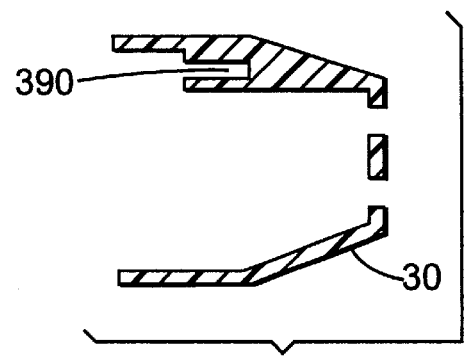
FIG. 26 is a cross-sectional view of a distal tip end, according to an embodiment of the invention.

As shown in the FIG. 26 embodiment, distal end 30 of ejector tube 5 defines a molded socket or groove 390 for receiving and holding in place an inserted rod or wire. Socket or groove 390 may be disposed on the exterior or the interior of ejector tip 5 according to the disposition of the rod or wire. The rod or wire is constructed of a material that holds its shape when bent, to maintain the shape of tube 340 as it is manipulated to achieve various shapes or configurations. It can be inserted into socket or groove 390 before the tip is assembled to the ejector tube, according to one embodiment.

Figure 27:
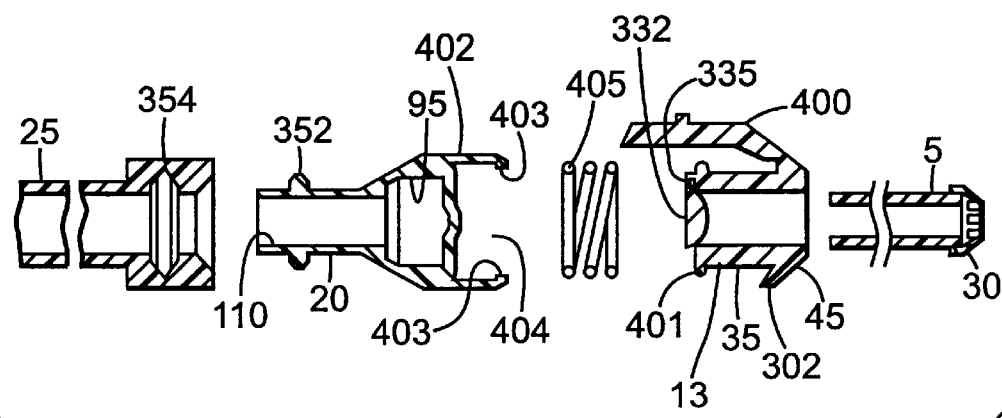
FIG. 27 is a cross-sectional, exploded view of a dental suction system according to an alternative embodiment of the invention.
Figure 28:
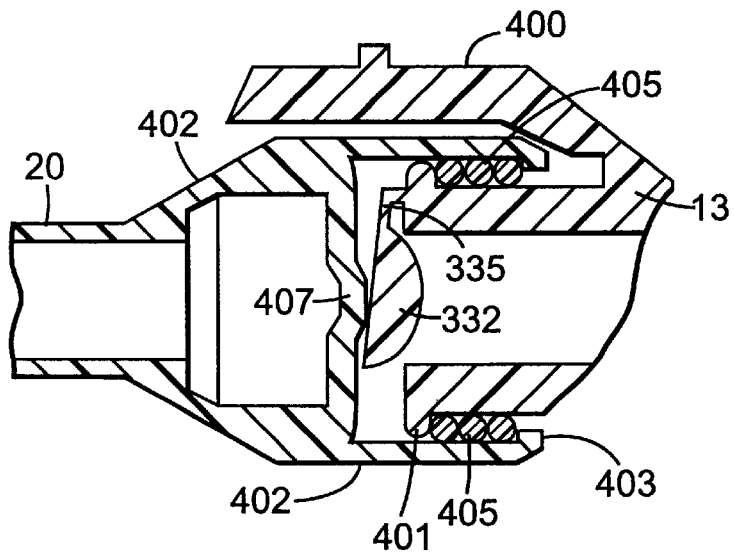
FIG. 28 is an enlarged cross-sectional view of a portion of FIG. 27.

According to the embodiment of FIGS. 27–28, a dental suction system of the invention includes an actuated valve design, allowing the on/off switch and/or valve at the main vacuum system to be eliminated if desired. Disposable ejector tip 5 includes an on/off valve incorporated into it. The valve has a mechanism for opening the valve to allow for flow of air and fluids from a patient's mouth to the main vacuum system holding tank or dispersion system. Distal portion 13 of the backflow prevention device in this embodiment comprises handle 400 and stop tabs 401. Main body cap 20 comprises slider arms 402, which define channel 404 and have stop tabs 403 disposed at their ends. Main body cap 20 slides with respect to distal portion 13 by use of handle 400. Interengagement of stop tabs 401 and 403 prevents disconnection of cap 20 and distal portion 13.

This embodiment includes a suitable valve device, such as sealing flap 332 connected to distal portion 13 by outwardly biased arm 335. Spring 405, disposed between stop tabs 401, 403, pulls distal portion 13 into main body cap 20. Consequently, center rib 407 engages sealing flap 332, which is biased towards center rib 407 by arm 335. As vacuum or spring 405 holds the valve shut, center rib 407 puts pressure on the center of flap 332, holding it in the sealing position against distal portion 13. When suitable vacuum pressure is applied and/or when handle 400 is moved, however, sealing flap 332 opens, as shown in FIG. 28. The amount of vacuum pressure needed to open sealing flap 332 varies, depending on the relative position of main body cap 20 with respect to distal portion 13 as manually moved/controlled by handle 400, e.g. by the patient. The patient can move handle 400 to change the configuration, i.e. the relative positioning of cap 20 and distal portion 13, to control suction to the patient's mouth.

As shown in FIG. 27 and later figures, the system includes quick-disconnect tab 352 and corresponding socket 354, to allow quick connection and disconnection between main body cap 20 and vacuum source or related structure 25.

Figure 29:
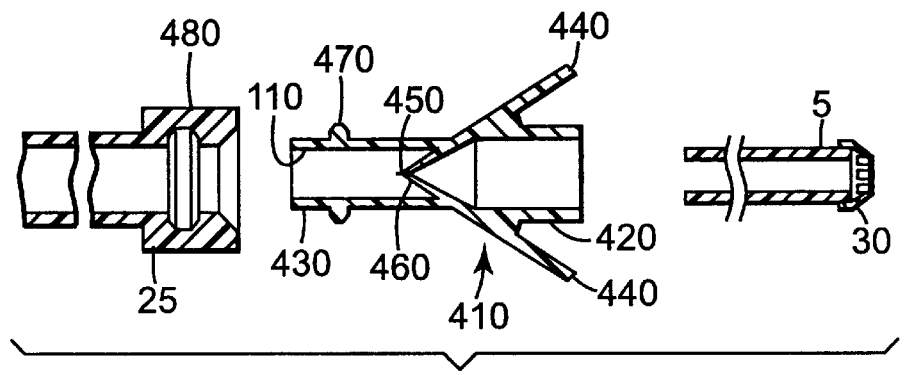
FIG. 29 is a cross-sectional, exploded view of a dental suction system according to an alternative embodiment of the invention.
Figure 29A:
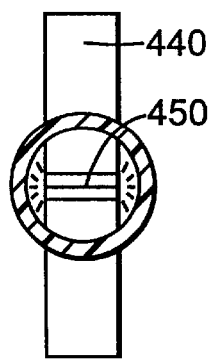
FIG. 29A is a front cross-sectional view of a portion of the FIG. 29 system.
Figure 30:
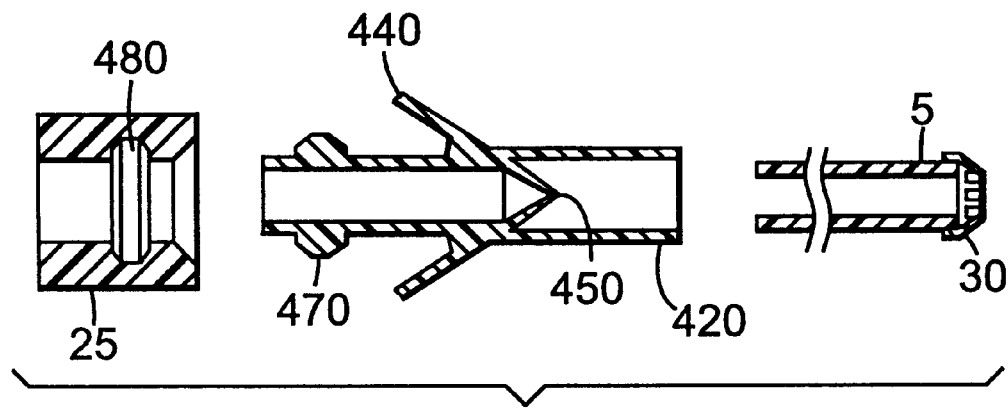
FIG. 30 is a cross-sectional, exploded view of a dental suction system according to an alternative embodiment of the invention.

Another embodiment allowing user control or manipulation of the valve is shown in FIGS. 29–30. According to this embodiment, valve member 410 is in fluid communication with and optionally one-piece with ejector tip 5, and is placed in fluid communication with vacuum source/device 25. Valve member 410 comprises distal end 420, proximal end 430, lever sections 440, and sealing area 450. The proximal ends of lever sections 440 converge to form lineal contact at sealing area 450, as shown in the front view of FIG. 29A. Valve member 410 thus comprises an elastic valve that remains shut at sealing area 450 until lever sections 440 are squeezed toward each other by the user. This squeezing motion tends to cause sealing area 450 to move to an open position, such that fluids may pass through valve member 410. In other words, squeezing the main valve body causes a leak to develop in the seal created in sealing area 450. Squeezing valve member 410 thus allows air, fluids and other matter to flow into the main vacuum system, including along the central longitudinal axis of the backflow-prevention device, as with previous embodiments. When the main valve body is not squeezed, on the other hand, backflow is prevented by the reverse-angled area depicted at 460.

Lever sections 440 and the remainder of valve member 410 are constructed of rigid, semi-rigid, or elastic material; the properties of the materials can be chosen to create an optimal sealing force. Alternatively, sealing area 450 also can be constructed to be partially open under normal vacuum pressure, but fully opened when a user depresses lever sections 440.

Valve member 410 also comprises structure for attachment to vacuum apparatus 25; for instance, ring 470 of valve member 410 is disposed on proximal end 430 so as to make a substantially sealed snap fit within ring seat 480.

FIG. 30 shows an additional squeeze valve embodiment, similar to that shown in FIG. 29. The structure and function of this valve is similar to that of FIG. 29, but sealing area 450 is at the proximal end of valve member 410 instead of the distal end. Vacuum helps to pull the seal shut and clear off fluid and debris, making for a good seal.

Figure 31:
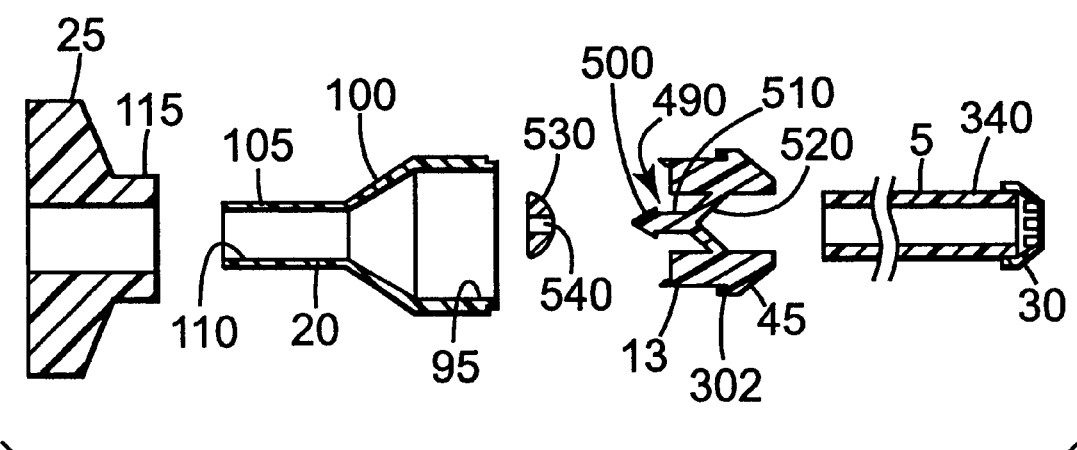
FIG. 31 is a cross-sectional, exploded view of a dental suction system according to an alternative embodiment of the invention.
Figure 32:
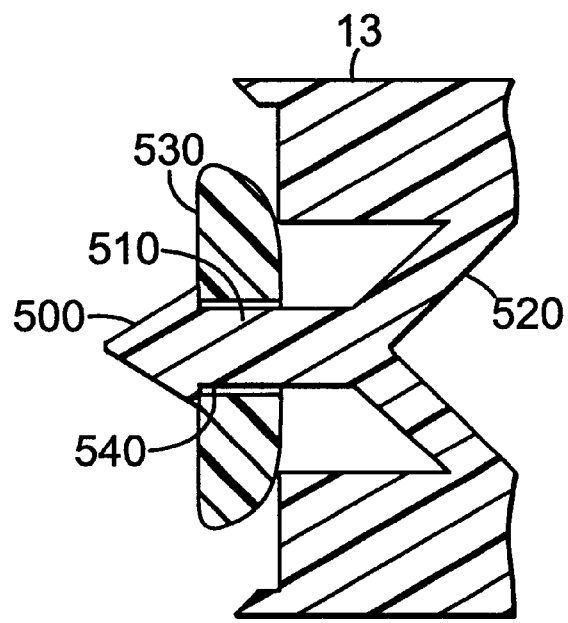
FIG. 32 is an enlarged, cross-sectional view of a portion of FIG. 31.

Additional use of elastic or substantially elastic materials to create a seal according to embodiments of the invention will now be described with respect to FIGS. 31–33. Such materials may be used in a variety of ways to create a seal that is opened by normal operating vacuum pressure but otherwise remains closed and prevents backflow. For instance, referring to FIGS. 31–32, distal portion 13 of the backflow prevention device includes frame 490 defining a substantially pointed tip 500 attached to neck 510. Neck 510 is attached to mounting arms 520, which are connected to and extend inwardly from the interior walls of distal portion 13.

Elastic flap 530 defines mounting aperture 540 extending therethrough, for being pushed over tip 500 into a substantially secured disposition with respect to neck 510. Elastic flap 530 creates a seal against distal portion 13 when there is insufficient vacuum pressure, but opens with respect to distal portion 13 when normal system vacuum pressure is applied. Elastic flap 530 becomes deformed and flexes when the vacuum pressure is increased so that fluid may pass around the flap and into the main waste system. Elastic flap 530 is depicted in a hemispherical shape, but other shapes may also be used. Further, a variety of materials with a wide range of deformative or compressive strength may be used. Also, such a valve may be augmented by other biasing means to create a seal; for instance, a spring or another deformable member may be incorporated into the device.

Figure 33:
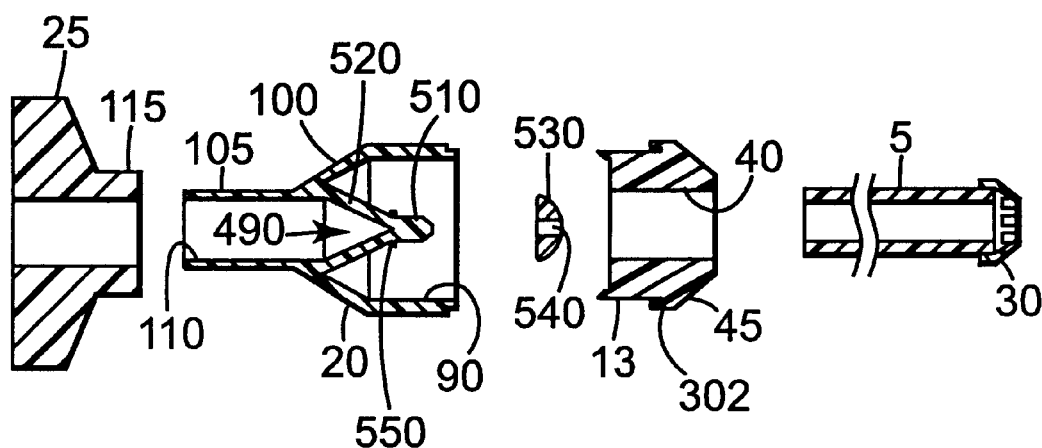
FIG. 33 is a cross-sectional, exploded view of a dental suction system according to an alternative embodiment of the invention.

In the FIG. 33 embodiment, elastic flap 530 is mounted within main body cap 20 instead of distal portion 13 of the backflow prevention device. Main body cap 20 thus includes frame 490 defining substantially pointed tip 500 attached to neck 510. Neck 510 is attached to mounting arms 520, which are connected to and extend inwardly from the interior walls of distal portion 13. Flap mount rings 550 create an abutment against or friction fit within elastic flap 530, to secure flap 530 with respect to frame 490. Alternatively, other means such as tabs, grooves, adhesives or other fastening mechanisms may be used, in this and other embodiments described and contemplated herein.

In operation, elastic flap 530 creates a seal with the face of distal portion 13 so that backflow is prevented. Adequate vacuum pressure from vacuum source 25 causes elastic flap 530 to deform and flex so that fluid and other material passes around the flap and into the main waste system. Other structural and functional features are as with respect to previously described embodiments.

Figure 34:
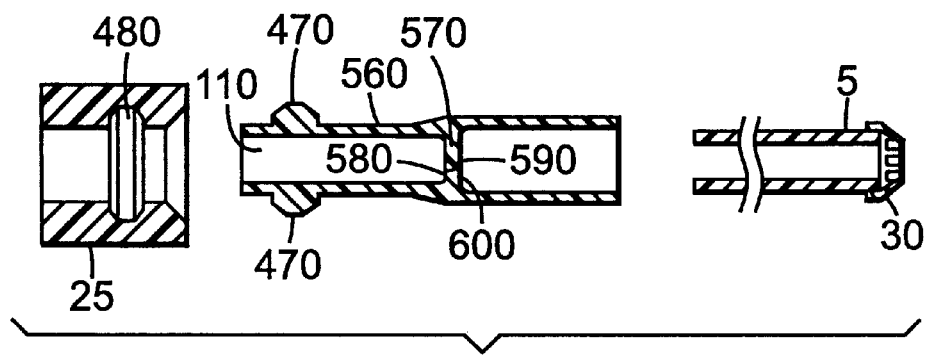
FIG. 34 is a cross-sectional, exploded view of a dental suction system according to an alternative embodiment of the invention.

According to the FIG. 34 embodiment, valve member 560 comprises hinged flap 570. Hinged flap 570 is created, according to the illustrated embodiment, by making cut 580 of about 330 degrees through center wall 590. The precise angle can depend on the material used to create flap 570. Hinged flap 570 thus meets abutment portion 600 of center wall 590 at cut 580 and is prevented from moving past it toward the distal end of the device. Therefore, any tendency of fluid or other material to flow back toward tip 5 tends to close the valve and prevent backflow, but normal vacuum pressure tends to open the valve to allow removal of material to the main waste system or equivalent.

Thus, as shown in FIG. 34 and others, a backflow prevention device is operably connected to the dental ejector tip to receive fluid therefrom, the backflow prevention device comprising valve componentry, the valve componentry comprising a hinged flap and an abutment portion. The hinged flap is biased toward the abutment portion within the backflow prevention device to form a substantial seal in the absence of substantial vacuum pressure and to prevent contaminant backflow upon release of vacuum, the hinged flap moving away from the abutment portion upon application of vacuum to allow fluid flow toward the vacuum source. The abutment portion comprises a raised portion extending inwardly from an interior wall of the backflow prevention device. The backflow prevention device defines a longitudinal axis, and the abutment portion and the hinged flap contact each other along contact surfaces thereof, the contact surfaces being generally parallel to each other and extending at an acute angle relative to the longitudinal axis. The acute angle preferably is about 30 degrees. The abutment portion extends no more than halfway across the internal diameter of the backflow prevention portion, according to the illustrated embodiment.

Figure 35:
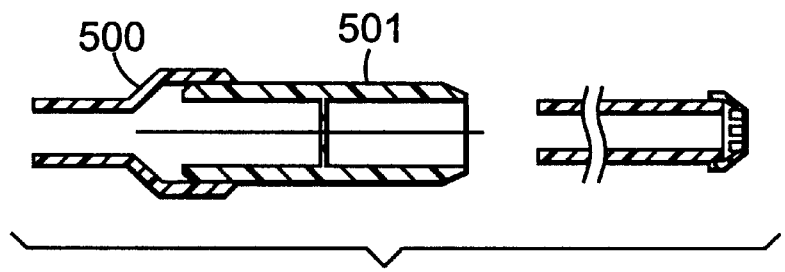
FIG. 35 is a cross sectional, exploded view of a dental suction system according to an alternative embodiment of the invention.

The embodiment of FIG. 35 is similar to that of FIG. 34. Proximal portion 605 of this figure or any of the other figures can be a quick de-coupler, or used as an adapter on a daily or permanent basis. It can be made of metal, plastic or other material facilitating normal handling and cleaning for dental devices.

Figure 36:
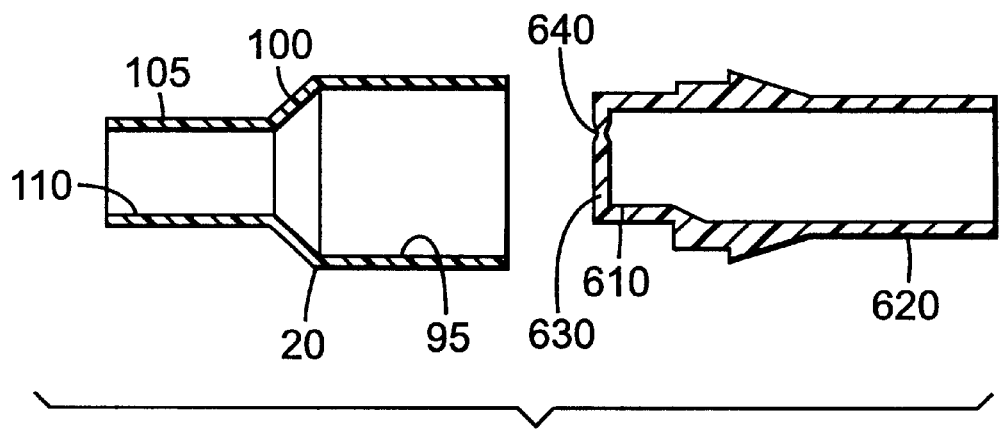
FIG. 36 is a cross-sectional, exploded view of a dental suction system according to an alternative embodiment of the invention.

According to the FIG. 36 embodiment, slit 610 in the side of valve body insert 620 causes hinged valve flap 630 to open when sufficient vacuum is present. The exact positioning of slit 610 along insert 620 is chosen to allow the valve to open under normal operating conditions. Indents or "bending aids" 640 optionally are provided, e.g. to force flap 630 to bend in a certain direction and at a certain location, as well as to allow flap 630 to open more easily. Insert 620 is akin to, connected to or one-piece with distal portion 30, and preferably is inserted within main body cap 20. Abutment portion 612 defines a contact surface extending generally perpendicular to a longitudinal axis of valve body insert 620.

Thus, according to the embodiments in FIGS. 35–36 and others, the backflow prevention device is received within a main body, and the hinged flap includes an outer wall of the backflow prevention device and extends across an internal diameter of the backflow prevention device.

An air-flow indicator, e.g., a molded arrow, can be used to indicate airflow direction in any of the embodiments contemplated by the invention. The indicator can be disposed on the outside of neck portion 45 of backflow-prevention device 10, for example, or at any other desired portion of the system. Additionally, a moisture-detection indicator can be included in backflow-prevention device 10 to indicate when moisture passes through it. For example, backflow-prevention device 10 can be formed of or can include a color-change material so that internal moisture is indicated by an external color change.

The various elements of the invention can be formed of multiple molded plastic parts. As alternatives to plastic, other moldable or even non-moldable materials demonstrating sufficient rigidity, for example polypropylene, polyethylene, various thermal elastomers, and other engineering polymers/plastics, can be used. Spring steel can be used, for example to construct base 210 and/or legs 215, 220 of spring assembly 80. According to one embodiment, the material can be impregnated with a germicide or other anti-bacterial substance, to further reduce the dangers associated with cross-contamination. The various components can be of either permanent or disposable construction.

While the invention has been described with reference to specific embodiments, the description is illustrative and is not to be construed to be limiting the scope of the invention. For example, features of the various described embodiments can be mixed and matched to suit a particular application. As one example, spring 145 in the embodiment of FIGS. 3 and 4 can be used in place of resilient element 195 in the embodiment of FIGS. 5 and 6, and vice versa. Componentry 15 in its various described forms is interchangeable between the various embodiments. Further, according to the invention, backflow of fluid contaminants can be prevented in a wide variety of dental, medical and other environments. Still further, although elements of the invention are illustrated as separate parts, one or more of the illustrated elements can be made as one-piece with each other, to reduce manufacturing costs and ease assembly. Thus, main body cap 20, backflow prevention device 10 (including distal portion 13), and/or tip 5 together can be a readily disposable one-piece structure to prevent cross contamination. According to one embodiment, these components are molded as one piece. Still further, embodiments of the invention are not limited to situations involving boundary-layer backflow, discussed above. Embodiments of the invention substantially eliminate backflow and the resulting cross-contamination in the vacuum line in a wide variety circumstances and applications. Various other modifications and changes may occur to those skilled in the art without departing from the spirit and scope of the invention.

What is claimed is:

1. A method of eliminating cross-contaminants in a dental suction system, the method comprising:
   providing a dental ejector tip constructed for insertion into a patient's mouth and removal of fluid contaminants therefrom upon application of a vacuum from a vacuum source;
   providing a backflow prevention device operably connected to the dental ejector tip, free of a valve member between the backflow prevention device and the dental ejector tip, to receive fluid therefrom upon application of vacuum from the vacuum source, the backflow prevention device comprising:
   a distal portion having an inlet;
   a proximal portion having an outlet; and
   valve componentry disposed within the backflow prevention device between the inlet and the outlet, the valve componentry being constructed to substantially prevent contaminant backflow upon release of vacuum from the vacuum source;

disconnecting the dental ejector tip and the backflow prevention device from the vacuum source;

disposing of the dental ejector tip and the backflow prevention device; and connecting a second dental ejector tip and a second backflow prevention device with the vacuum source.

2. The method of claim 1, wherein the dental ejector tip and the backflow prevention device are disconnected and disposed of as a unit.

3. The method of claim 1, further comprising providing a vacuum tube operably connected to the backflow prevention device to receive fluid therefrom upon application of vacuum from the vacuum source.

4. The method of claim 3, further comprising disconnecting the vacuum tube from the vacuum source, disposing of the vacuum tube, and connecting a second vacuum tube with the vacuum source.

5. The method of claim 1, wherein the backflow prevention device comprises a distal housing portion directly connected to the dental ejector tip, the dental ejector tip and the distal housing portion being constructed to provide direct fluid communication therebetween at all times.

6. The method of claim 1, wherein the valve componentry comprises a valve seat, a seating mechanism and a biasing member, the biasing member being constructed to bias the seating mechanism toward the valve seat when vacuum is released.

7. The method of claim 6, wherein the biasing member comprises a flange extending toward the seating mechanism.

8. The method of claim 1, wherein the valve componentry comprises a blocking mechanism constructed and arranged to automatically block contaminant backflow upon release of vacuum from the vacuum source.

9. The method of claim 1, the valve componentry comprising opposed portions each being biased toward each other within the backflow prevention device to form a substantial seal in the absence of substantial vacuum pressure and to prevent contaminant backflow upon release of vacuum, the opposed portions each moving away from each other upon application of vacuum to allow fluid flow toward the vacuum source.

10. The method of claim 1, the valve componentry comprising a flap portion, a neck portion operably coupled with the flap portion at a substantially central area of the flap portion, and structure defining a surface that the flap engages to form a substantial seal in the absence of substantial vacuum pressure and to prevent contaminant backflow upon release of vacuum, the flap moving away from the surface upon application of vacuum to allow fluid flow toward the vacuum source.

11. The method of claim 1, the backflow prevention device comprising a disposable on/off valve.

12. The method of claim 1, wherein the backflow prevention device is one-piece with the dental ejector tip.

13. A dental apparatus backflow prevention system for substantially preventing contaminant backflow into a patient's mouth, the system comprising:

a saliva ejector tube for insertion into a patient's mouth and removal of fluid therefrom upon application of a vacuum;

a backflow prevention device operably connected to the saliva ejector tube to receive the fluid therefrom, the backflow prevention device comprising:

a distal portion having an internal valve seat;

a proximal portion coupled with the distal portion and constructed for operative connection to a vacuum source, said distal and proximal portions forming a housing with an inlet formed in the distal portion and an outlet formed in the proximal portion, the housing being constructed such that the vacuum source draws fluid within the housing only from the inlet to the outlet; and valve componentry disposed within the backflow prevention device, the valve componentry comprising:

a biasing member operably coupled with the housing; and a seating mechanism operably supported by the housing to be biased by the biasing member to automatically engage the valve seat and prevent contaminant backflow upon release of vacuum, the seating mechanism automatically disengaging from the valve seat and allowing fluid flow toward the vacuum source upon application of the vacuum;

wherein the biasing member comprises a plurality of sprung, bendable legs constructed to bias the seating mechanism toward the valve seat, each leg including at least one notch.

14. A dental apparatus backflow prevention system for substantially preventing contaminant backflow into a patient's mouth, the system comprising:

a saliva ejector tube for insertion into a patient's mouth and removal of fluid therefrom upon application of a vacuum;

a backflow prevention device operably connected to the saliva ejector tube to receive the fluid therefrom, the backflow prevention device comprising:

a distal portion;

a proximal portion coupled with the distal portion and constructed for operative connection to a vacuum source, said distal and proximal portions forming a housing with an inlet formed in the distal portion and an outlet formed in the proximal portion, the housing being constructed such that the vacuum source draws fluid within the housing from the inlet to the outlet, one of the distal and proximal portions supporting an internal valve seat; and valve componentry disposed within the backflow prevention device, the valve componentry comprising:

a biasing member operably coupled with the housing; and a seating mechanism operably supported by the housing to be biased by the biasing member to automatically engage the valve seat to define a plane of contact and prevent contaminant backflow upon release of vacuum, the seating mechanism automatically disengaging from the valve seat and allowing fluid flow toward the vacuum source upon application of the vacuum;

wherein the seating mechanism includes an engagement member defining a curved shape for engaging the valve seat in the plane of contact the curved shape also extending through the plane of contact, further wherein the biasing member comprises a lever arm extending away from the engagement member.

15. The system of claim 14, wherein the engagement member is one-piece with the lever arm.

16. A dental ejector tip for substantially preventing contaminant backflow into a patient's mouth, the dental ejector tip comprising:

a saliva ejector tube for insertion into a patient's mouth and removal of fluid therefrom upon application of a vacuum;

a backflow prevention device operably connected to the saliva ejector tube, free of a valve member between the backflow prevention device and the saliva ejector tube, to receive the fluid therefrom, the backflow prevention device comprising:
a distal portion having an inlet, the distal portion being directly connected to the saliva ejector tube at the inlet, the saliva ejector tube and distal portion being constructed to provide direct fluid communication from the patient's mouth to the inlet at all times;
a proximal portion having an outlet, the proximal portion being coupled with the distal portion and constructed for readily removable connection at the outlet to a vacuum source, the distal portion and the proximal portion being constructed such that the vacuum source draws fluid within the housing only from the inlet to the outlet, the distal portion and the proximal portion defining a valve chamber; and
valve componentry disposed within the backflow prevention device, the valve componentry automatically preventing contaminant backflow upon release of vacuum and automatically allowing fluid flow toward the vacuum source upon application of the vacuum, the valve componentry comprising a valve seat, an engagement member defining a curved shape for engaging the valve seat, and a biasing member comprising a lever arm extending away from the engagement member to bias the engagement member toward the valve seat;
wherein the ejector tip comprising both the saliva ejector tube and the backflow prevention device is constructed for detachment from the vacuum source and disposal as a unit between patients.

17. A dental apparatus backflow prevention system for substantially preventing contaminant backflow into a patient's mouth, the system comprising:
a dental ejector tip for insertion into a patient's mouth and removal of fluid therefrom upon application of a vacuum from a vacuum source; and
a backflow prevention device operably connected to the dental ejector tip to receive the fluid therefrom, the backflow prevention device comprising valve componentry, the valve componentry comprising opposed portions each being biased toward each other within the backflow prevention device to form a substantial seal in the absence of substantial vacuum pressure and to prevent contaminant backflow upon release of vacuum, the opposed portions each moving away from each other upon application of vacuum to allow fluid flow toward the vacuum source, the opposed portions extending outwardly beyond an outer shell of the backflow prevention device for manual manipulation.

18. The system of claim 17, wherein the opposed portions each flare outwardly upon application of vacuum to allow fluid flow toward the vacuum source.

19. The system of claim 17, wherein the opposed portions are constructed to move away from a central axis of the backflow prevention device and to allow fluid flow along the central axis upon application of vacuum.

20. The system of claim 17, wherein the opposed portions extending outwardly beyond the outer shell are constructed to allow the patient to manually affect flow from the patient's mouth.

21. The system of claim 20, wherein the opposed portions extending outwardly beyond the outer shell are lever sections constructed to be squeezed toward each other to manually affect flow from the patient's mouth.

22. The system of claim 17, wherein the dental ejector tip is one-piece with the backflow prevention device.

23. A dental apparatus backflow prevention system for substantially preventing contaminant backflow into a patient's mouth, the system comprising:
a dental ejector tip for insertion into a patient's mouth and removal of fluid therefrom upon application of a vacuum from a vacuum source; and
a backflow prevention device operably connected to the dental ejector tip to receive the fluid therefrom, the backflow prevention device comprising valve componentry, the valve componentry comprising a hinged flap and an abutment portion, the hinged flap being biased toward the abutment portion within the backflow prevention device to form a substantial seal in the absence of substantial vacuum pressure and to prevent contaminant backflow upon release of vacuum, the hinged flap moving away from the abutment portion upon application of vacuum to allow fluid flow toward the vacuum source the backflow prevention device further comprising indents, operably coupled with the hinged flap, to allow the hinged flap to open more easily.

24. The system of claim 23, wherein the abutment portion comprises a raised portion extending inwardly from an interior wall of the backflow prevention device.

25. The system of claim 24, wherein the backflow prevention device defines a longitudinal axis, further wherein the abutment portion and the hinged flap contact each other along contact surfaces thereof, the contact surfaces being generally parallel to each other and extending at an acute angle relative to the longitudinal axis.

26. The system of claim 25, wherein the acute angle is about 30 degrees.

27. The system of claim 23, wherein the abutment portion extends no more than halfway across the internal diameter of the backflow prevention portion.

28. The system of claim 23, wherein the backflow prevention device is received within a main body; further wherein the hinged flap includes an outer wall of the backflow prevention device and extends across an internal diameter of the backflow prevention device.

29. A dental apparatus backflow prevention system for substantially preventing contaminant backflow into a patient's mouth, the system comprising:
a dental ejector tip for insertion into a patient's mouth and removal of fluid therefrom upon application of a vacuum from a vacuum source; and
a backflow prevention device operably connected to the dental ejector tip to receive the fluid therefrom, the backflow prevention device comprising valve componentry, the valve componentry comprising a hinged flap and an abutment portion, the hinged flap being biased toward the abutment portion within the backflow prevention device to form a substantial seal in the absence of substantial vacuum pressure, the abutment portion being coplanar with the flap when said substantial seal is formed, and to prevent contaminant backflow upon release of vacuum, the hinged flap moving away from the abutment portion upon application of vacuum to allow fluid flow toward the vacuum source, wherein the abutment device extends no more than halfway across the internal diameter of the backflow prevention portion.

* * * * *